United States Patent [19]

Gregory

[11] Patent Number: 6,106,546
[45] Date of Patent: Aug. 22, 2000

[54] INDUCING VASODILATION

[75] Inventor: Kenton W. Gregory, Boston, Mass.

[73] Assignee: The General Hospital Corporation, Boston, Mass.

[21] Appl. No.: 08/991,095

[22] Filed: Dec. 15, 1997

Related U.S. Application Data

[63] Continuation of application No. 08/365,311, Dec. 27, 1994, which is a continuation of application No. 08/219,243, Mar. 29, 1994, abandoned, which is a continuation of application No. 08/099,001, Jul. 23, 1993, abandoned, which is a continuation of application No. 07/836,189, Feb. 13, 1992, abandoned, which is a continuation of application No. 07/419,035, Oct. 10, 1989, abandoned, which is a continuation-in-part of application No. 07/255,813, Oct. 11, 1988, abandoned.

[51] Int. Cl.$^7$ .............................. A61B 17/36; A61B 5/00
[52] U.S. Cl. ................................. 607/89; 606/7; 606/15
[58] Field of Search ................................ 606/14, 15, 16, 606/17, 7, 10, 11, 12; 607/88, 89

[56] References Cited

U.S. PATENT DOCUMENTS

| | | |
|---|---|---|
| 4,418,688 | 12/1983 | Loeb . |
| 4,512,762 | 4/1985 | Spears . |
| 4,782,818 | 11/1988 | Mori . |
| 4,790,310 | 12/1988 | Ginsburg et al. . |
| 4,829,262 | 5/1989 | Furamoto . |
| 4,834,093 | 5/1989 | Littleford et al. . |
| 4,862,886 | 9/1989 | Clarke et al. . |
| 5,321,715 | 6/1994 | Trost .......................................... 372/69 |
| 5,500,012 | 3/1996 | Brucker et al. ............................. 606/7 |
| 5,571,151 | 11/1996 | Gregory .................................... 607/88 |
| 5,573,531 | 11/1996 | Gregory .................................... 606/14 |
| 5,649,923 | 7/1997 | Gregory .................................... 606/15 |
| 5,728,091 | 3/1998 | Payne et al. ............................... 606/7 |
| 5,733,277 | 3/1998 | Pallarito .................................... 606/7 |
| 5,755,714 | 5/1998 | Murphy-Chittorian .................... 606/7 |
| 5,776,127 | 7/1998 | Anderson et al. ......................... 606/15 |
| 5,817,144 | 10/1998 | Gregory .................................... 607/89 |
| 5,832,013 | 11/1998 | Vessik et al. .............................. 372/26 |
| 5,860,972 | 1/1999 | Hoang ....................................... 606/15 |

FOREIGN PATENT DOCUMENTS

| | | |
|---|---|---|
| 0192833 | 9/1986 | European Pat. Off. . |
| 0244557 | 11/1987 | European Pat. Off. . |
| 8606269 | 11/1986 | WIPO . |

OTHER PUBLICATIONS

Bell et al., "Laser–Induced High Pressure Shock Waves in Water", Applied Physics Letters, vol. 10, No. 2, Jan. 15, 1967, pp. 46–48.

Carome et al., "Photographic Studies of Laser–Induced Pressure Impulses in Liquids", Applied Physics Letters, vol. 11, No. 2, Jul. 15, 1967, pp. 64–66.

Barnes et al, "Laser Induced Underwater Sparks", Applied Physics Letters, vol. 13, No. 8, Oct. 15, 1968, pp. 282–284.

Linde et al., "Shock waves in Solids", Scientific American, May 1969, pp. 83–91.

Felix et al., "Laser–Induced Liquid Breakdown–a Step–by–Step Account", Applied Physics Letters, vol. 19, No. 11, Dec. 1, 1971, pp. 484–487.

Ready, John F., "Material Processing–An Overview", Proceedings of the IEEE, vol. 70, No. 6, Jun. 1982, 533–544.

Fujimoto et al., "Time–Resolved Studies of Nd: YAG Laser–Induced Breakdown", Investigative Ophthalmology and Visual Science, vol. 26, No. 12, Dec. 1985, pp. 1771–1777.

Vogel et al., "Cavitation Bubble Dynamics and Acoustic Transient Generation in Ocular Surgery with Pulsed Neodymium: YAG Lasers", Ophthalmology, vol. 93, No. 10, Oct. 1986, pp. 1259–1269.

Teng et al, "Microsecond–Long Flash Photography of Laser– Induced Ablation of Bilary and Urinary Calculi", Lasers in Surgery and Medicine, vol. 7, Jun. 1987, pp. 394–397.

Prince et al., "Preferential Ablation of Calcified Arterial Plaque with Laser–Induced Plasmas", IEEE Journal of Quantum Electronics, vol. QE–23, No. 10, Oct. 1987, pp. 1783–1786.

Prince et al., "Pulsed Laser Ablation of Calcified Plaque", SPIE vol. 906 Optical Fibers in Medicine III, Jan. 13–16, 1988, pp. 305–309.

Ehrreich et al., "Relaxation of Mammalian . . . Ultraviolet Radiation", Nature, vol. 218, May 18, 1968, pp. 682–684.

Furchgott et al., "The Photoactivated Relaxation of Smooth Muscle of Rabbit Aorta", *The Journal of General Physiology*, vol. 44, 1961, pp. 499–519.

Gal et al., "Vascular Spasm Complicates . . . Pulsed Laser Irradiation", American Heart Assoc., *Circulation*, 1987.

Steg et al., "Effects of Continuous Wave Laser . . . Contraction and relaxation", American Heart Association., *Circulation*, 1987.

*Primary Examiner*—Linda C. M. Dvorak
*Assistant Examiner*—Sonya Harris-Ogugua
*Attorney, Agent, or Firm*—Majestic, Parsons, Siebert & Hsue P.C.

[57] ABSTRACT

A method for inducing dilation of a blood vessel, e.g., of an obstructed blood vessel, includes irradiating the vessel with a pulse of light or its equivalent at a low energy fluence.

44 Claims, No Drawings

INDUCING VASODILATION

CROSS-REFERENCE TO RELATED APPLICATIONS

This is a continuation of copending application Ser. No. 08/365,311, filed Dec. 27, 1994, which is a continuation of application Ser. No. 219,243, filed Mar. 29, 1994, now abandoned, which is a continuation of application Ser. No. 08/099,001, filed Jul. 23, 1993, now abandoned, which is a continuation of application Ser. No. 07/836,189, filed Feb. 13, 1992, now abandoned, which is a continuation of application Ser. No. 07/419,035, filed Oct. 10, 1989, now abandoned, which is a continuation-in-part of application Ser. No. 07/255,813, filed Oct. 11, 1988, now abandoned, all of which are hereby incorporated herein by this reference.

BACKGROUND OF THE INVENTION

This invention relates to treatment of vascular obstruction.

A fixed obstruction within a blood vessel, for example, an atherosclerotic plaque or an atheroembolus, can reduce blood flow to a level inadequate to provide for the metabolic demand of tissues supplied by the blood vessel. Vasospasm of an artery can produce similar problems because of partial or complete obstruction of an artery which otherwise appears normal. The combination of such dynamic or spastic constriction at the point of a clinically benign fixed obstruction can create a clinically severe reduction of flow. Vasospasm can occur spontaneously, or because of environmental stimuli, including either pharmacologic stimuli, for example, ergonovine testing, and mechanical stimuli, e.g., contact with a surgical instrument, or a diagnostic or therapeutic catheter as a complication of percutaneous transluminal catheter angioplasty.

Approaches proposed for treating vascular obstruction include inducing or causing vasodilation. They also include removing or reducing the size of a fixed obstruction to partially or fully relieve the obstruction and permit restoration of a sufficient blood flow. Examples of these approaches include pharmacotherapeutic treatments and mechanical procedures. J. B. Young et al., "Medical Options in Chronic Stable Angina," *Cardiovascular Medicine,* July, 1985, pp. 21–30.

Pharmacotherapeutic treatments for angina include administration of nitrates. These dilate peripheral vessels and reduce resistance in the coronary circulation. Nitrates, however, are not always effective, and some people suffer intolerable side effects.

Mechanical procedures for relieving stenoses in which an occlusive lesion, e.g., an atheroslerotic plaque, is present include bypass surgery and percutaneous transluminal angioplasty (PTA). PTA includes balloon angioplasty, where the plaque and intima of the vessel are mechanically displaced by inflation of a balloon. The balloon is positioned in the lumen of the vessel at the stenosis. Not all patients can benefit from balloon angioplasty.

The mechanical procedures also include laser thermal angioplasty, where plaque formations are ablated by irradiation with laser energy. Laser thermal angioplasty is an inappropriate treatment for vasospasm where no fixed obstruction is present to be ablated. Moreover, severe vasospasm, refractory to pharmaceutical dilators, can be a complication of continuous wave laser thermal angioplasty.

An example of use of the combination of a dilation catheter and a laser is provided by Littleford, U.S. Pat. No. 4,834,093. A laser is used to ablate tissue so that a balloon catheter can be subsequently inserted within the remaining tissue and inflated to displace the vessel tissue.

DovGal et al., Abstract 2085 of the 60th Scientific Sessions, Circulation 1987, describe use of a pulsed laser (at 12 MJ/pulse, 10–80 Hz) rather than a continuous laser in order to avoid problems of vasoconstriction or vasospasm.

SUMMARY OF THE INVENTION

I have discovered that a prompt long-lasting (several hours or more) vasodilation can result from irradiating a vessel wall with a light energy pulse having an energy fluence below the threshold for inducing vasospasm or for damaging the vessel wall. Such vasodilation can be obtained by any means able to create a shock wave similar to that produced by this light energy including, e.g., an acoustic, ultrasonic or hydraulic wave generator.

In general, the invention features a method for inducing dilation of a blood vessel, e.g., of an obstructed vessel, including subjecting the vessel to a shock wave equivalent to irradiating the vessel with a pulse of light at an energy fluence below the energy fluence threshold for causing vasoconstriction in such a vessel. Such energy fluence levels are readily measured by any standard procedure, for example by subjecting a chosen vessel to various fluences, and selecting a fluence below one that causes vasoconstriction.

The dilation can occur along a length upstream and downstream of the point of irradiation. Dilation occurs promptly after the irradiation, providing practically immediate relief from the obstruction. The treated vessel can remain dilated for several hours or longer, relieving an emergency condition that may have been presented by the obstruction, and allowing ample time for application of other therapies. The vessel can be treated from within or from outside the vessel wall.

In preferred embodiments, the method includes irradiating the vessel with a pulse of light at a low energy fluence; irradiating the vessel with a succession of such pulses of light, each at a low energy fluence; the energy fluence is below the threshold for inducing vasospasm, or below the threshold for thermally damaging the wall of the vessel; the energy fluence is between 1 and 30 $J/cm^2$ (dependent upon wavelength of the light used, and absorption coefficients of the medium around the vessel, and the vessel itself), most preferably less than 15 $J/cm^2$, more preferably less than 10 $J/cm^2$, and even more preferably less than 5 $J/cm^2$; the duration of each pulse is between about 250 nanoseconds and about 300 microseconds, most preferably between 500 nanoseconds and 100 microseconds, even more preferably about 1 microsecond. One of ordinary skill in this field understands that the effect of the light can be varied dependent upon tissue absorption characteristics and the wavelength of the incident seam.

In other embodiments, the step of irradiating the vessel with a pulse of light includes directing a beam of light onto the vessel; the beam of light is generated by a laser, preferably by a pulsed laser; the step of directing the beam of light includes directing the light through a light guide, such as a fiber optic bundle.

In other embodiments, the method further includes the step of administering a pharmaceutical dilator. In preferred embodiments the pharmaceutical dilator is administered prior to, following, or concurrently with the step of irradiating the vessel with the pulse of light.

In other embodiments, the method further includes carrying out a transluminal angioplasty in the vessel near the site of irradiating.

Because the dilation can result in an increase in vessel diameter to a size greater than that of the vessel at baseline tonus, the method of the invention can be used for treating a vessel in which the flow of blood is blocked by a fixed obstruction within the vessel, and in which there is no elevated tonus of the vessel wall. Moreover, the method of the invention can be used where the stenosis is caused by vasoconstriction alone, and in those instances in which a vasoconstriction combines with a fixed obstruction to cause the blockage. For example, the method of the invention can be used to open at least a narrow lumen in cases where balloon angioplasty or laser angioplasty is indicated, but in which the vessel is so tightly stenosed that a catheter or even a guidewire cannot be passed through; after the vessel is dilated by the method of the invention sufficiently to permit the guidewire or catheter to pass, traditional angioplasty can be applied to ablate the obstruction.

Other features and advantages of the invention will be apparent from the following description of preferred embodiments thereof, and from the claims.

DESCRIPTION OF THE PREFERRED EMBODIMENTS

Vasodilation can be induced according to the invention by directing a pulse of light energy, or its equivalent, at a wavelength in the spectral range including UV, visible, and IR wavelengths, having a low energy fluence, onto a vessel wall at a site near an obstruction.

Conveniently the energy is produced by a laser, and most conveniently it is produced by a laser capable of producing pulses, such as a flashlamp-excited dye laser.

The effect also can be produced by a non-laser source capable of creating a similar effect by, for example, an acoustic, ultra-sonic or hydraulic wave generator. Such a device is designed to mimic the effect of laser light on blood, and its subsequent effect on the vascular endothelium and smooth muscle. Those of ordinary skill in the art recognize that an acoustic or mechanical wave induced by light absorption of red blood cells is readily measured, analyzed and reproduced. Such reproduction provides equivalent means to induce vasodilation. The advantage of using such alternatives means is that the desired effect can be less expensively reproduced, thereby reducing the cost of the over-all procedure.

The following example describes a method of the invention and one particular use of it; the example is presented for purposes of illustration, and is not intended to limit the claims.

EXAMPLE

This example illustrates inducing vasospasm and vasodilation in femoral arteries of rabbits by pulsed laser irradiation at high and low energy fluences, respectively.

Radiation at 480, 504 and 577 nm was delivered in 1–20μ second pulses at various energy fluences by an optical fiber to the femoral arteries of each of 22 New Zealand white rabbits as follows. A side branch of the femoral artery was opened and a conventional 320 μm diameter optical fiber introduced, by way of the side branch, into the femoral artery, and oriented approximately perpendicular to the femoral artery wall. A succession of 20 laser pulses were delivered to the site on the wall at a repetition rate of 2 Hz and at energy fluences ranging from 1 to 20 millijoules (mJ) per pulse. The diameter of the vessel and the flow through it were continuously monitored by ultrasound throughout the treatment.

At energy fluences greater than about 15 $J/cm^2$ per pulse, focal vasospasm, i.e., vasoconstriction at the irradiation site, occurred. The vasospasm progressed to complete vessel occlusion, which persisted for times of between 15 and 120 min. Intravasal administration of $MgSO_4$ ameliorated this higher energy laser pulse-induced vasospasm, and raised the energy threshold for vasospasm. Intravasal administration of nitroglycerin had no effect. The effect was variable at energy fluences between about 10 and about 15 $J/cm^2$; in some instances vasoconstriction resulted, while in other instances vasodilation resulted.

At energy fluences about 10 $J/cm^2$ per pulse and lower, the irradiation induced a dramatic increase in vessel diameter, extending over a portion of the vessel proximally and distally from the irradiation site. This lower energy induced vasodilation persisted for times as much as 4 hours or longer after the irradiation was stopped, and persisted despite attempts to induce systemic vasoconstriction. Each of 18 vessels irradiated at energy fluences about 5 $J/cm^2$ per pulse were dilated, showing an average increase in diameter of 66% over baseline tonus.

Other pulse durations (full width at half maximum), and optical fibers of other dimensions can be used. One of ordinary skill in the art will appreciate that the energy density delivered at the site will depend upon the pulse duration, laser power, and fiber geometry; and these and other variables can be selected or adjusted without undue experimentation to achieve the desired energy fluence.

Vasodilation has been observed when delivering laser pulses at similar energy fluences to sites in coronary arteries in dogs, both in vessels at normal tone and in vessels with thrombosis, or somewhat elevated vascular tone.

The dilation effect can be initiated immediately following a single pulse, and it continues as a succession of pulses are delivered. The energy fluences are selected to be below the energy threshold for damage to the particular tissues being treated. Such thresholds can be readily measured using the technique described above.

Any suitable source of light energy can be used, so long as it can be regulated to generate pulses of suitable duration and low energy. Conventional dye lasers are convenient, such as for example a Candela flashlamp-excited dye laser.

In the above example, the energy was directed perpendicularly onto the vessel, because that was a convenient approach for repeated treatment of the femoral artery. Any direction, however, can be used.

The observed effect appears to be independent of light interaction with smooth muscle. Exposure of rabbit femoral arteries in vivo to the laser energy described above while the vessel is immersed in saline or perfused with saline did not result in vasodilation. When the saline was replaced by blood, however, prompt vasodilation occurred during radiant exposure. This implies that the vasodilation described herein is the result of laser energy interaction with blood rather than smooth muscle. I propose, without being bound to any theory, that light interaction with blood results in vaporization and de facto detonation of blood elements. This produces a secondary acoustic and mechanical wave, probably as a result of complex cavitary or vapor bubble formation. The acoustic or mechanical-hydraulic wave causes release of vessel spasm. This release may be caused by a mechanical separation of the arterial wall, an increase in endothelial sensed shear forces which then stimulates an increase in a locally released endothelial derived smooth muscle relaxant (EDRF).

The dilation effect can be produced when energy is directed at the vessel from outside the vessel, that is, either directly or through other tissues onto the outer surface of the vessel wall. Suitable wavelengths can be selected, in particular, wavelengths longer than 480 nm, when using such an external approach, to ensure adequate penetration of the light or equivalent energy to the vessel wall itself.

Where a succession of pulses is used, any repetition rate can be used, provided the pulses do not overlap such that the effective fluency is elevated above the threshold for vasoconstriction, or for damage to the vessel wall.

The method of the invention can be used for dilating a vessel that has an occlusion not treatable by angioplasty. For example, a vessel can be treated that is constricted by elevated vessel wall tonus, as for example by vasospasm, at a location where no fixed obstruction is contained within the vessel. The method of the invention can be used with known pharmaceutical dilators, for example, nitrates such as nitroglycerin, to provide a cooperative effect of the light energy or equivalent pulse, and the pharmaceutical dilator.

The method of the invention also can be used for dilating a vessel that contains a fixed obstruction, such as for example an atherosclerotic lesion or a thrombus, at the location of the occlusion. Where a stenosis results from a combination of a fixed obstruction within the vessel and an elevated wall tonus, the method of the invention can be used to relieve the stenosis at least to the extent that elevated tonus contributes to the occlusion. Moreover, because the method of the invention can result in dilation of a vessel to a size greater than its size at baseline tonus, the method can prove useful in increasing the vessel diameter and at least partially opening the vessel lumen even in circumstances where there is no elevated tonus at the location of the occlusion.

The method of the invention also can be used in combination with other known therapies. For example, it can be used as an adjunct to conventional angioplasty, for example, in circumstances where balloon angioplasty or laser angioplasty could be employed, but where the stenosis restricts the vessel lumen so tightly that a conventional guidewire or transluminal catheter cannot pass the stenosis. In such a circumstance the vessel can be illuminated according to the invention, and then when the vessel has dilated sufficiently to allow the instruments to pass, the angioplasty can be carried out.

Vessels treated according to the invention can have an elevated energy threshold for laser-induced vasospasm for a time after irradiation. Thus, the method of the invention can be used to treat a vessel before laser angioplasty, to reduce the likelihood that vasospasm may result from the higher laser energies used for ablating the obstruction.

The method of the invention also can be used, for example, in combination with laser-mediated clot removal, for example, in laser coronary thrombolysis, as a treatment for acute myocardial infarction. Increasing the vessel diameter near the locus of the clot can aid in relieving the obstruction, and also provides a prompt increase in blood flow at the site.

The method of the invention also can be used for treatment of vasospastic arterial disorders such as Raynauds phenomenon, which involves peripheral arterial vasospasm at the extremities, and potentially vasospastic disorders of the cerebrovascular system.

Other embodiments are included within the following claims.

I claim:

1. A method of treating a blood vessel having an obstruction at a locus therein, comprising:

directing a pulse of light energy within the vessel near the locus of the obstruction, said pulse of light energy of an energy density below a predetermined threshold for damage to the vessel and sufficient to generate a mechanical-hydraulic wave within the vessel; and monitoring the treatment during said directing.

2. The method of claim 1 wherein the energy density is between 1 and 30 J/cm$^2$.

3. The method of claim 1 wherein the energy density is below 15 J/cm$^2$.

4. The method of claim 1 wherein the energy density is below about 10 J/cm$^2$.

5. The method of claim 1 wherein the energy density is below about 5 J/cm$^2$.

6. The method of claim 1 wherein the light energy is provided by a laser.

7. The method of claim 6 wherein the laser is a pulsed laser.

8. The method of claim 6 wherein said directing provides an interaction between the laser-provided light energy and blood within the vessel.

9. The method of claim 1 wherein the mechanical-hydraulic wave results from cavitary or vapor bubble formation.

10. The method of claim 1 wherein said directing includes directing through a light guide.

11. The method of claim 1 wherein said directing includes directing through an optical fiber or a fiber optic bundle.

12. The method of claim 1 wherein a duration and a power of the light energy pulse and a geometry of the light guide are selected to provide the energy density desired.

13. The method of claim 1, further comprising administering a pharmaceutical agent before, during or after said directing.

14. The method of claim 13 wherein the pharmaceutical agent is administered before or during said directing and acts cooperatively with the pulse of light energy.

15. The method of claim 1 wherein the light energy is infrared energy.

16. The method of claim 1 wherein the light energy is of a wavelength selected from a group consisting of 480, 504 and 577 nanometers.

17. The method of claim 1 wherein a duration of the pulse is between about 250 nanoseconds and about 300 microseconds.

18. The method of claim 1 wherein a duration of the pulse is between 500 nanoseconds and 100 microseconds.

19. The method of claim 1 wherein a duration of the pulse is from 1 to 20 microseconds.

20. The method of claim 1 wherein a duration of the pulse is about 1 microsecond.

21. The method of claim 1 wherein said directing includes directing a succession of pulses of light energy.

22. The method of claim 21 wherein the pulses number 20.

23. The method of claim 21 wherein the pulses are delivered at a repetition rate such that the pulses are non-overlapping.

24. The method of claim 21 wherein the pulses are delivered at a repetition rate of 2 Hertz.

25. The method of claim 21 wherein the light energy ranges from 1 to 20 millijoules per pulse.

26. A method of treating a blood vessel having an obstruction at a locus therein, comprising:

directing a succession of pulses of laser light energy within the vessel near the locus of the obstruction through a light guide, each pulse of an energy density of between 1 and 30 J/cm$^2$, said directing providing an interaction between the laser light energy and blood within the vessel and forming a cavitary or vapor bubble sufficient to generate a mechanical-hydraulic wave within the vessel; and monitoring the treatment during said directing.

27. The method of claim 26 wherein the energy density is below 15 J/cm$^2$.

28. The method of claim 26 wherein the energy density is below about 10 J/cm$^2$.

29. The method of claim 26 wherein the energy density is below about 5 J/cm$^2$.

30. The method of claim 26 wherein the laser light energy is provided by a pulsed laser.

31. The method of claim 26 wherein said directing includes directing through an optical fiber or a fiber optic bundle.

32. The method of claim 26 wherein a duration and a power of the pulse of laser light energy and a geometry of the light guide are selected to provide the energy density desired.

33. The method of claim 26, further comprising administering a pharmaceutical agent before, during or after said directing.

34. The method of claim 33 wherein the pharmaceutical agent is administered before or during said directing and acts cooperatively with the pulse of laser light energy.

35. The method of claim 26 wherein the laser light energy is infrared energy.

36. The method of claim 26 wherein the laser light energy is of a wavelength selected from a group consisting of 480, 504 and 577 nanometers.

37. The method of claim 26 wherein a duration of the pulse is between about 250 nanoseconds and about 300 microseconds.

38. The method of claim 26 wherein a duration of the pulse is between 500 nanoseconds and 100 microseconds.

39. The method of claim 26 wherein a duration of the pulse is from 1 to 20 microseconds.

40. The method of claim 26 wherein a duration of the pulse is about 1 microsecond.

41. The method of claim 26 wherein the pulses number 20.

42. The method of claim 26 wherein the pulses are delivered at a repetition rate such that the pulses are non-overlapping.

43. The method of claim 26 wherein the pulses are delivered at a repetition rate of 2 Hertz.

44. The method of claim 26 wherein the laser light energy ranges from 1 to 20 milliJoules per pulse.

* * * * *